US009132183B2

(12) United States Patent
Sirigireddy et al.

(10) Patent No.: US 9,132,183 B2
(45) Date of Patent: *Sep. 15, 2015

(54) **MODIFIED LIVE (JMSO STRAIN) *HAEMOPHILUS PARASUIS* VACCINE**

(75) Inventors: Kamesh R. Sirigireddy, Worthington, MN (US); Paulraj K. Lawrence, Worthington, MN (US); Russell F. Bey, Worthington, MN (US); Randy R. Simonson, Worthington, MN (US)

(73) Assignee: NEWPORT LABORATORIES, Worthington, MN (US)

( * ) Notice: Subject to any disclaimer, the term of this patent is extended or adjusted under 35 U.S.C. 154(b) by 717 days.

This patent is subject to a terminal disclaimer.

(21) Appl. No.: 13/385,303

(22) Filed: Feb. 13, 2012

(65) Prior Publication Data

US 2012/0225091 A1 Sep. 6, 2012

Related U.S. Application Data

(63) Continuation-in-part of application No. 11/648,390, filed on Dec. 28, 2006, now Pat. No. 8,404,253.

(51) Int. Cl.
*A61K 39/102* (2006.01)
*A61K 39/00* (2006.01)
*C12R 1/21* (2006.01)
*C07K 14/285* (2006.01)
*C12N 9/12* (2006.01)
*C12N 9/14* (2006.01)

(52) U.S. Cl.
CPC ............ *A61K 39/102* (2013.01); *C07K 14/285* (2013.01); *C12N 9/1205* (2013.01); *C12N 9/14* (2013.01); *C12R 1/21* (2013.01); *C12Y 207/01059* (2013.01); *C12Y 306/03014* (2013.01); *A61K 2039/522* (2013.01); *A61K 2039/542* (2013.01); *A61K 2039/552* (2013.01)

(58) Field of Classification Search
None
See application file for complete search history.

(56) References Cited

U.S. PATENT DOCUMENTS

| 7,749,518 | B2 * | 7/2010 | Masignani et al. | 424/256.1 |
|---|---|---|---|---|
| 8,350,018 | B2 * | 1/2013 | Bensaid et al. | 536/23.7 |
| 8,404,253 | B2 * | 3/2013 | Oliveira et al. | 424/256.1 |
| 8,617,574 | B2 * | 12/2013 | Von Gabain et al. | 424/256.1 |
| 8,652,773 | B2 * | 2/2014 | Bakaletz et al. | 435/6.15 |
| 2010/0255035 | A1 * | 10/2010 | Oliveira et al. | 424/256.1 |
| 2012/0225091 | A1 * | 9/2012 | Sirigireddy et al. | 424/190.1 |
| 2014/0004144 | A1 * | 1/2014 | Bey et al. | 424/201.1 |
| 2015/0098968 | A1 * | 4/2015 | Lawrence et al. | 424/256.1 |

FOREIGN PATENT DOCUMENTS

WO   WO 2008/085406 A2 *   7/2008

OTHER PUBLICATIONS

Oliveira et al (Vet. Microbiol., 2004, 99/1:1-12).*
Hooke et al (Lancet, 1985, 1/844:1472-1474).*
Linde et al (Archiv. Fur Experimentelle Veterinarmedizin, 1978, 32/6:943-949).*

* cited by examiner

*Primary Examiner* — Nita M Minnifield
(74) *Attorney, Agent, or Firm* — Judy Jarecki-Black; Chad Kitchen; Merial, Inc.

(57) ABSTRACT

The present invention is a live vaccine from a culture of cells of *Haemophilus parasuis* exhibiting attenuated pathogenicity and capable of triggering a protective immune response when administered to pigs. The cell culture was modified from a pathogenic parent strain by MNNG mutagenesis and was selected by complete dependence on streptomycin for growth. Several SNPs have been identified as associated with specific proteins that are associated with virulence as seen in the literature in *H. parasuis* or related bacterial species.

22 Claims, No Drawings

MODIFIED LIVE (JMSO STRAIN) HAEMOPHILUS PARASUIS VACCINE

This patent application is a continuation-in-part of U.S. patent application Ser. No. 11/648,390, filed Dec. 28, 2006, now U.S. Pat. No. 8,404,253 with the title "Modified Live (JMSO Strain) Haemophilus parasuis Vaccine."

BACKGROUND OF THE INVENTION

Haemophilus parasuis is an early colonizer of the upper respiratory tract of pigs. Non-virulent strains of this organism can be normally isolated from the nasal cavity, tonsil, and trachea of healthy pigs. Virulent strains of H. parasuis can also invade the host and cause systemic lesions characterized by fibrinous polyserositis, arthritis and meningitis.

Recent studies have demonstrated that non-virulent strains are more prevalent in the upper respiratory tract than virulent strains. However, even though the majority of pigs are colonized by non-virulent H. parasuis strains, they are not protected against systemic infection by virulent strains. It is widely recognized in the vaccine field that live vaccines may sometimes provide a higher degree and broader range of protective immunity than killed vaccines.

Controlled exposure to a low dose of live, virulent H. parasuis may reduce nursery mortality more efficiently than vaccination using commercial or autogenous killed products. However, exposure to live virulent bacteria poses significant risk of the very disease one is trying to protect against. Attenuation of the virulence of the vaccine strain in a way that is stable and also retains the immunogenicity of the live organism is therefore highly desirable to vaccine development.

Although neither the mechanisms involved in the protective immunity following controlled exposure, nor the identity of antigens which provide protective immunity, are clear at this time, it is known that protective immunity can be induced by such exposure. Moreover, pigs with controlled exposure to live H. parasuis are protected against homologous challenge through intratracheal and intraperitoneal routes, suggesting that exposed pigs develop local immune response (upper respiratory tract) as well as a systemic response. Live organisms undergo limited replication in the host at sites of infection and may thereby elicit additional arms of the immune response (e.g., local immunity) and/or augment the level of the response.

H. parasuis killed vaccines (commercial or autogenous) are known to generate poor cross-protection against different serovars. This may be due to incomplete expression of potential virulence factors when this organism is grown in vitro. Live organisms are more likely to express a wide variety of proteins and factors required for growth in vivo. Iron-regulated outer membrane proteins (IROMPS) are an example of potential virulence factors that may be expressed in vivo, but are rarely expressed in vitro. A modified live vaccine would be capable of expressing virulence factors when administered to a host. Most likely this product would induce a more involved immune response creating the potential for a safe, more efficacious vaccine.

The pork industry is in need of a safe and efficacious product capable of aiding the prevention of disease due to multiple serotypes of H. parasuis.

SUMMARY OF THE INVENTION

The present invention provides a vaccine which provides cross-serovar protection for pigs against infection by H. parasuis, comprising an immunologically effective amount of live cells of a strain derived from a pathogenic parent strain of the organism, which are dependent upon streptomycin for growth, and which cells exhibit attenuated pathogenicity compared to those of the parent strain but which are capable of triggering an immune response that protects the animals against infection when administered as a live vaccine, and a veterinarily acceptable carrier. The present invention also provides identification of certain genes that have undergone single nucleotide polymorphisms (SNPs) in the attenuated strain. The present invention also conceptually identifies the protein products that are produced by the genes which show these SNPs, based on correlation of polynucleotide sequence with the complete genome of a standard strain (SH0165) of serovar 5 of H. parasuis and analysis of SNPs that resulted in amino acid changes. Vaccines of the invention may further comprise one or more other components including, for example, an adjuvant.

A principle object and advantage of the present invention is that it is a vaccine that provides cross-serovar protection for pigs against infection by H. parasuis.

Another principle object and advantage of the present invention is that several SNPs in genes that encode known proteins and result in amino acid changes in the mutant strain as compared with a standard serovar 5 H. parasuis strain have been identified. The changes in the amino acids in these proteins may be responsible for the decreased virulence of the mutant strain as compared with the parent strain.

DETAILED DESCRIPTION OF THE PREFERRED EMBODIMENT

Applicants have discovered that cells of a pathogenic strain of H. parasuis may be attenuated, and that the resulting attenuated cells are capable of triggering an immune response that protects pigs against H. parasuis infection when administered as a live vaccine.

The term "attenuated" as used herein describes a cell, culture, or strain of H. parasuis exhibiting a detectable reduction in infectivity or virulence in vivo as compared to that of the parent strain of H. parasuis from which the attenuated cell, culture, or strain is derived. Reduction in virulence encompasses any detectable decrease in any attribute of virulence, including infectivity in vivo, or any decrease in the severity or rate of progression of any clinical symptom or condition associated with infection.

The present invention further encompasses preparation and use in a vaccine of cells of a strain of H. parasuis derived from a pathogenic parent strain of H. parasuis and which exhibit attenuated pathogenicity compared to cells of the parent strain and which are capable of triggering an immune response that protects pigs against H. parasuis infection.

The live attenuated cells of the invention are capable of triggering an immune response that protects pigs against H. parasuis infection after one or more administrations as a live vaccine. A "protective immune response" is defined as any immunological response, either antibody or cell mediated immunity, or both, occurring in the pig that either prevents or detectably reduces subsequent infection, or eliminates or detectably reduces the severity, or detectably slows the rate of progression, of one or more clinical symptoms or conditions associated with H. parasuis infection. The term "immunologically effective amount" refers to that amount or dose of vaccine or antigen that triggers a protective immune response when administered to the pig.

Example 1

Identification of the Parent Strain

The parental strain has been identified as serovar 5, *H. parasuis*; Newport Laboratories reference no. 3-0930-1.

The isolate was received by Newport Laboratories from Iowa State University Veterinary Diagnostic Laboratory as an agar slant labeled *H. parasuis* 1888 on May 2, 2003. The isolate was identified as *H. parasuis* based on biochemical reactions (non-hemolytic, v-factor dependent, urea, and arabinose negative). The isolate was identified as a serovar 5, *H. parasuis* by the Faculty of the Veterinary Medicine Department of the University of Montreal.

Example 2

Development of the Vaccine Strain (a) Procedures used to attenuate the parental strain: Attenuation of the parent strain was accomplished by chemical mutagenesis with N-methyl-N'-nitroso-N-nitrosoguanidine (MNNG) and selection for growth dependence on media containing 400 micrograms per mL streptomycin sulfate.

The protocol for MNNG mutagenesis was adapted from Lopes et al., 2001. The parent strain was initially checked for purity by inoculating the culture on 5% sheep blood agar containing a nurse *Staphylococcus* sp. streak and incubating for 24 h at 37° C.+−2° C. in a candle jar.

The culture was pure, based on the absence of extraneous growth outside the *Staphylococcus* sp. streak and growth of the *H. parasuis* satellite colonies in the area adjacent to and just outside the streak. After purity was confirmed, the parent *H. parasuis* strain was swabbed on chocolate agar plates. Plates were incubated as indicated above.

The resulting bacterial cells were harvested by adding 1 mL of PBS to the chocolate agar plate and scraping colonies using a sterile, modified Pasteur pipet (heated and bent to the shape of a hockey stick).

Bacterial cells were pooled to one side of the plate, and an automated PIPET-AID® and a 5 mL pipet were used to collect the cell suspension. The cell suspension was then diluted in pre-warmed PPLO media (BD) containing MNNG (Sigma-Aldrich Cp., St. Louis, Mo., 30 micrograms/mL). The mixture of cells and MNNG was then incubated at 37° C.+/−2° C. for 30 minutes without agitation. Following incubation, bacteria were collected by centrifugation and washed with cold phosphate-buffered saline (PBS), pH 7.4, to eliminate residual mutagen. The washed cells were resuspended in pre-warmed PPLO media and incubated at 37° C.+/−2° C. for 40 min.

The MNNG-exposed bacteria were plated onto PPLO agar plates containing 400 mcg/mL streptomycin sulfate and onto PPLO without streptomycin sulfate and both sets of plates were incubated at 37° C.+/−2° C. for 24 hours in a candle jar. PPLO agar plates without streptomycin sulfate were used to ensure the MMNG treatment did not inactivate all bacterial cells.

Following incubation, the plates without streptomycin showed bacterial growth, confirming that the MNNG treatment did not inactivate all bacterial cells. A single colony was observed and harvested from a single PPLO plate containing streptomycin sulfate. This colony was passed to a PPLO agar plate and PPLO broth, both supplemented with 400 mcg/mL streptomycin sulfate (permissive media), and to PPLO broth and agar plate containing no streptomycin sulfate (non-permissive). Cultures were incubated as above. Growth on permissive medium and lack of growth on non-permissive medium was seen. This was the basis for selection of the modified live, streptomycin-dependent, *H. parasuis* vaccine strain. The attenuated *H. parasuis* strain and proposed Master Seed has been identified, "*Haemophilus parasuis* streptomycin dependent Master Seed 101304".

The selected Master Seed has proven to be avirulent for the natural host of *H. parasuis* (pigs) in preliminary research. A backpassage study of 4 passes with two pigs per pass was completed.

Two pigs were inoculated intraperitoneally with 3 cc of $10^9$ cells of the streptomycin dependent strain. Two days following inoculation, pigs were euthanized and intraperitoneal fluids were collected and passed to 2 additional pigs. This was done for a total of 4 passes. Animals were observed for clinical signs following inoculation and for clinical lesions following euthanasia. Tissues and swabs were taken from euthanized pigs and isolation of the vaccine strain and potential revertant strain was attempted. Approximately 1 mL of the subcultured peritoneal fluid was tested at Newport Laboratories for *H. parasuis* isolation (as above) and by *H. parasuis* detection PCR.

Following the administration of the vaccine strain in the backpassage and safety studies, no clinical signs associated with disease caused by *H. parasuis* were noticed in any pigs. All isolation attempts for the vaccine strain and the streptomycin-independent revertant strain were negative. *H. parasuis* detection PCR from peritoneal fluid from the preliminary backpassage study was negative.

(b) Screening methods and protocols for the identification and purification of the vaccine microorganism: The vaccine microorganism was selected based on its complete dependence on streptomycin. Purity of the vaccine strain was done according to the guidelines set forth in 9 CFR 113.27(d) and reported in the Master Seed report submitted Aug. 31, 2005.

Identification of the vaccine strain was confirmed based on biochemical reactions, dependency on streptomycin sulfate, *H. parasuis* detection PCR, *H. parasuis* Genotyping PCR, gram staining, and colony morphology. Summary for all testing was reported in the Master Seed Report submitted to USDA-CVB Mar. 23, 2006.

Both the parent and vaccine have been shown to be viable by the American Type Culture Collection (ATCC) and the following ATCC accession numbers have been assigned:

| | |
|---|---|
| *Haemophilus parasuis*: Parent JMSO 50703 | PTA-7710 |
| *Haemophilus parasuis*: JMSO 10134 | PTA-7711 |

Example 3

Vaccine Production

The vaccine culture was started from a working seed. The working seed was subcultured to X+5 by using PPLO media supplemented with 400 mcg/mL streptomycin, 2% dextrose, 10% horse serum, and 0.2% NAD was used. The final subculture was incubated at approximately 37° C. overnight with agitation. Following incubation, the culture was centrifuged for 20 minutes at 3,000 rpms. The cell pellet was resuspended in fresh PPLO media with 1/10 of the original volume. The vaccine was stored on ice until used. Immediately prior to vaccination, Trigen was added to the vaccine at 10% of the resuspended volume. Prior to vaccination, the vaccine was titrated and cell concentrations were determined. Cell concentration for the first vaccination was $10^7$ to $10^{9.60}$ CFUs per mL. The vaccine used for animals receiving 2 doses was prepared in the same manner. Cell concentration for the $2^{nd}$ vaccination was $10^{9.55}$ CFU per mL.

Example 4

Efficacy of the Vaccine (a) Methods

At arrival, all pigs were injected with 0.3 mL of Excede IM and housed in the same room at the Research Farm (RF) for 7 days. To assure equal representation in treatment groups, pigs were randomly allotted based on litters. Prior to vaccination, non-vaccinated pigs, pigs receiving the vaccine orally, and pigs receiving the vaccine IM were housed in three separate rooms. Pigs receiving a single dose were separated from pigs receiving a $2^{nd}$ dose by a solid partition. Pigs were vaccinated at approximately 4 weeks of age; pigs receiving a second dose were revaccinated 2 weeks following the first vaccination. Three weeks after the $2^{nd}$ vaccination, all pigs were challenged.

To challenge the pigs, a single ampoule of the *H. parasuis* parent strain, Newport Laboratories, was removed from frozen storage and streaked on 5 chocolate agar plates. Plates were incubated at 37° C. in candle jars for approximately 48 hours. Using a sterile cotton swab, growth was harvested and used to inoculate 400 mL of PPLO media containing the following supplements: 10% horse serum, 2% dextrose (50%), and 0.2% NAD per mL of PPLO. Cultures were incubated at 37° C. on a shaker cart for approximately 6 hours. Following incubation, % transmittance was recorded, and cell titrations were made. All pigs were challenged intravenously and intraperitoneally with 1 mL per route.

All vaccinations were given at a rate of 0.2 mL per pig IM or orally as appropriate.

(b) Results

Rectal temperatures were taken prior to challenge and for 4 days following challenge. A temperature at or above 40.5° C. was considered a fever. Pigs were weighed prior to challenge, at the time of death or at the end of the study, as appropriate. Average Daily Gain (ADG) was determined for each pig and daily observations were made once daily by a blind observer.

Pigs were observed daily for clinical signs and were scored accordingly. A daily observation chart was constructed using the following scoring system.

| Score | Clinical Signs |
| --- | --- |
| 4* | Moribund or dead, unable to rise, lateral recumbancy, CNS signs. |
| 3 | Severely lame and or lethargic. Total or complete lameness on one or more limbs, cannot support weight. Extreme difficulty in rising, can stand when prompted, quick to lie down. |
| 2 | Moderately lame and/or lethargic. Lame but will support weight on lame leg, must be prompted to move |
| 1 | Mildly lethargic. Ears are down, not active, slow to rise and move. |
| 0 | Normal |

*Dead pigs are given 4 points for each experimental day following death.

A treatment was considered satisfactory, if, in a valid assay, 80% or more of the vaccinated pigs in the group survived challenge and showed no lesions upon necropsy and at least 80% of the non-vaccinated control pigs do not survive challenge and/or are positive for 1 or more lesions at necropsy. To confirm infection from *H. parasuis* following challenge, lung and heart samples, and peritoneal, joint, and pleural swabs from each necropsied pig were collected and sent to Newport Laboratories (NPL) diagnostic lab for *H. parasuis* isolation.

The test was valid as 100% of non-vaccinated pigs had lesions or did not survive challenge.

Experiment #1

Homologous Protection (Serovar 5 Vaccination Serovar 5 Challenge)

Table 1 shows the mortality rate after inoculation with the vaccine and subsequent challenge with the parent strain.

| Treatment Group | Mortality |
| --- | --- |
| Non-vaccinates | 100% |
| 1 dose IM vaccinates | 10% |
| 2 dose IM vaccinates | 0% |
| 1 dose oral vaccinates | 80% |
| 2 dose oral vaccinates | 100% |

Table 2 shows the percentage of pigs in each treatment group with a fever.

| Treatment Group | % of animals with a fever |
| --- | --- |
| Non-vaccinates | 90% |
| 1 dose IM vaccinates | 10% |
| 2 dose IM vaccinates | 0% |
| 1 dose oral vaccinates | 50% |
| 2 dose oral vaccinates | 70% |
| Non-vaccinated/non-challenged | 0% |

Table 3 shows the Average Daily Gain for each treatment group following challenge:

| Treatment Group | Average daily gain (loss) |
| --- | --- |
| Non-vaccinates | −2.88 lbs/day |
| 1 dose IM vaccinates | 1.65 lbs/day |
| 2 dose IM vaccinates | 1.71 lbs/day |
| 1 dose oral vaccinates | −2.85 lbs/day |
| 2 does oral vaccinates | −5.51 lbs/day |
| Non-vaccinated/non-challenged | 2.21 lbs/day |

Table 4 shows the total points (scores) registered from daily observations.

| Treatment Group | Total Points |
| --- | --- |
| Non-vaccinates | 116 |
| 1 dose IM vaccinates | 15 |
| 2 dose IM vaccinates | 13 |
| 1 dose oral vaccinates | 112 |
| 2 dose oral vaccinates | 137 |
| Non-vaccinated/non-challenged | 0 |

Experiment 2

Heterologous Protection (Serovar 5 Vaccination, Heterologous Challenge)

Table 5 shows the mortality % for each treatment group when challenged with a serovar 4 strain.

| Treatment group | Mortality |
|---|---|
| Non-vaccinates | 78% |
| 1 dose vaccinates | 0% |
| 2 dose vaccinates | 0% |

89% of non-vaccinated pigs were positive for one or more lesions commonly associated with H. parasuis infection. No vaccinated pigs were necropsied as no vaccinated pig met euthanasia criteria.

Table 6 shows the mortality % for each treatment group when challenged with a serovar 13 strain.

| Treatment group | Mortality |
|---|---|
| Non-vaccinates | 100% |
| 1 dose vaccinates | 13% |
| 2 dose vaccinates | 0% |

All non-vaccinated pigs were positive for 1 or more lesions. Two of 8 pigs vaccinated with a single dose were positive for one or more lesions. One of 8 pigs vaccinated with 2 doses was positive for 1 or more lesions.

All non-vaccinated pigs had fevers following challenge with the parent strain, while all vaccinated pigs had normal temperatures following challenge.

Table 7 shows the average daily gain for each treatment group when challenged by the serovar 5 parent strain, 3-09302-1.

| Treatment Group | Average Daily Gain (loss) |
|---|---|
| Non-vaccinates | −3.84 lbs/day |
| 1 dose vaccinates | 1.65 lbs/day |
| 2 dose vaccinates | 1.71 lbs/day |

Table 8 shows the total points (scores) for each treatment group when challenged by the serovar 5 parent strain, 3-09302-1.

| Treatment Group | Total Points |
|---|---|
| Non-vaccinates | 139 |
| 1 dose vaccinates | 0 |
| 2 dose vaccinates | 0 |

All non-vaccinated pigs had fevers following challenge with the parent strain, while all vaccinated pigs had normal temperatures following challenge.

Challenge with Serotype 4 Strain

All non-vaccinated pigs challenged with strain 4-1230-2 (type 4) had a fever for at least one day. No vaccinated pigs had fevers following challenge.

Table 9 shows the average daily gain for each treatment group following challenge with the serotype 4, 4-1230-2 strain.

| Treatment Group | Average Daily Gain (loss) |
|---|---|
| Non-vaccinates | −2.43 lbs/day |
| 1 dose vaccinates | 1.27 lbs/day |
| 2 dose vaccinates | 1.86 lbs/day |

Table 10 shows total points (scores) registered from daily observations were.

| Treatment Groups | Total Points |
|---|---|
| Non-vaccinates | 99 |
| 1 dose vaccinates | 0 |
| 2 dose vaccinates | 0 |

Challenge with Serotype 13 Strain

All non-vaccinated pigs challenged with strain 5-1124-23 (type 13) had a fever for at least one day following challenge. Four pigs from the 1 dose vaccinates had a fever for one or more days following challenge and 1 pig from the 2 dose vaccinates had a fever for one or more days.

Table 11 shows the average daily gain for each treatment group following challenge with the serotype 13, 5-1124-23 strain.

| Treatment Groups | Average Daily Gain (loss) |
|---|---|
| Non-vaccinates | −4.12 lbs/day |
| 1 dose vaccinates | 0.99 lbs/day |
| 2 dose vaccinates | 0.79 lbs/day |

Table 12 shows the total points (scores) registered from daily observations.

| Treatment Groups | Total Points |
|---|---|
| Non-vaccinates | 120 |
| 1 dose vaccinates | 15 |
| 2 dose vaccinates | 6 |

Discussion/Conclusions: The H. parasuis ML (modified live) vaccine had clear protection against all 3 challenge strains. Mortality, average daily gain, daily observations, and body temperature data all support the efficacy of and the potential for the ML vaccine to be used as a tool for controlling disease caused by H. parasuis. Results support the efficacy of the vaccine against heterologous challenge strains.

Example 5

Mutant Characterization Using DNA Sequencing

Materials and Methods:
PCR/Sequencing Primer Development:

The Haemophilus influenzae streptomycin resistance (strA) gene was used as a model for primer development as there was little published sequence data for H. parasuis. A freeware primer selection software was used to select primers for this gene.

```
strA Forward
                                      (SEQ ID NO: 13)
TAC GCA AAC CGC GTG TGA strA Reverse
                                      (SEQ ID NO: 14)
TGC GTG CTT CAA CAC TAC GA
```

Genomic DNA Extraction:
Cultures of the parent and the JMSO strain were swabbed onto multiple agar media (Chocolate agar for parent strain, PPLO agar with 400 mg/mL of streptomycin for the JMSO strain). Plates were incubated at 37° C.+/−3 in a candle jar until sufficient lawn of growth was obtained (approx. 48 hrs).

The Qiagen Genomic DNA extraction kit was used to obtain the DNA for sequencing. The method was as follows:

Aseptically, 5 mL of 0.25% Tryptic Soy Broth (TSB) was added to each plate. With a sterile loop, the growth was scraped off the agar surface, the plate was tipped to the side and the bacterial suspension was collected with a pipet and pooled into a tared centrifuge tube. The suspensions were centrifuged at 4,500 rpm for 10 min. The supernatant was decanted and the remaining pellet was weighed (for calculation of extraction lysis steps). Pelleted cells were frozen until lysis could be conducted.

Buffer B1 was prepared by adding 100 mg/mL solution of RNase A to obtain a final concentration of 200 g/mL. Eleven mL of Buffer B1 was added to the frozen pellets and the tubes vortexed until a uniform suspension was obtained. To the suspension, 300 ul of a lysozyme stock (100 mg/ml) and 500 ul of Proteinase K were added. The tubes were incubated at 37° C.+/−3 for 1 hr. The sample was deproteinized with Buffer B2, by adding 4 ml to the suspension. The tube was vortexed for a few seconds and then was placed in a water bath at 50° C. for 30 min.

A 500/G Genomic Tip (provided in the kit) was set up for each of the parent and DMSO digested pellets. The tips were equilibrated with 10 ml of Buffer QBT. The tip was emptied by gravity flow. The digested pellet was vortexed for 10 sec at maximum speed and diluted 1:1 with Buffer QBT. One half of the total volume of the digested pellet was poured into the Genomic Tip. A syringe plunger was used to apply positive pressure to help the eluation (20-40 drops/min maximum flow rate). The Genomic Tip was then washed twice with 15 ml of Buffer QC. The genomic DNA was then eluted into a sterile tube with 15 ml of Buffer QF. The DNA was then precipitated with 10.5 ml of room temperature isopropanol by mixing and centrifuging at >5000×g for 15 min. The supernatant was removed and the DNA pellet washed with 4 ml of cold 70% ethanol. The pellets were vortexed and the samples centrifuged briefly. The supernatant was carefully removed and the remaining DNA pellet was allowed to air dry for 5-10 minutes. The DNA pellet was resuspended in TE buffer (pH 8.0) and the DNA allowed to dissolve overnight at 37° C.+/−3.

The resuspended DNA was then evaluated using a 2% agarose gel. The evaluation revealed high molecular weight DNA. The DNA was then quantified using a UV Spectrophotometer for the PCR amplification.

Amplification of Target Gene:

Amplification of the strA gene was conducted on the genomic DNA samples. Approximately 20 ng of DNA was used in this reaction. The "per reaction mix" consisted of the following: 37.8 μl of sterile molecular grade water, 5.0 μl of Taq DNA polymerase buffer (provided with Taq), 1.0 μl of dNTP mix (100 μM each), 10 μM of each forward and reverse primers, and 0.2 μl of Taq DNA polymerase. The samples were amplified at the following conditions: 94° C. for 5 min., followed by 30 cycles of 94° C. for 30 sec., 54° C. for 20 sec., and 68° C. for 30 sec.

DNA Sequencing:

The PCR product was purified of residual dNTPs and Taq DNA polymerase in preparation for sequencing using the QIAQUICK® PCR Purification Kit (Qiagen). The purified PCR product was resolved on a 2% agarose gel, to estimate quantity for sequencing step.

A Dye Terminator Cycle Sequencing (DTCS) and a Beckman Coulter CEQ 8000 (Beckman Coulter) were used to sequence this product. The reaction was set up per the recommendations in the DTCS Quick Start Master Mix kit provided by Beckman Coulter. Forward and reverse sequence reactions were set up using 0.15 M of primer.

Results:

The sequencing parameters resulted in the complete strA gene. A BLAST search revealed that the sequence obtained was an exact match to the strA gene of *H. influenzae*. Both forward and reverse sequences were obtained, thru multiple repetitions. The sequences were analyzed using MegAlign (DNASTAR Inc, Madison, Wis.) software and a consensus sequence was obtained. The alignment and comparison of the parent and JMSO consensus sequences revealed two nucleotide changes, coding for two amino acid differences. Nucleotide 68: GCA(Alanine) parent to GAA(Glutamic Acid) JMSO strain. Nucleotide 272: CCG(Proline) parent to CTG (Leucine) JMSO.

The nucleotide and sequence data (SEQ ID NOS: 1-4) are identified in a sequence listing document filed with this application.

Example 6

Construction of Genomic Libraries and Characterization of SNPs

Log phase cultures of *H. parasuis* parent and mutant strains were pelleted separately by centrifuging at 10,000×g for 5 min. The pellet was used for genomic DNA isolation using Qiagen DNA mini kit as per manufacturer's instructions (Qiagen, Valencia, Calif.). The purified genomic DNA was visualized by using DNA electrophoresis technique and quantified in a spectrophotometer (Maniatis et al, Cold spring harbor laboratory). The genomic DNA was used in the preparation of a library for sequencing as per manufacturer's protocols (Illumina Genomic DNA Prep Kit, Illumina, San Diego, Calif.). The genomic DNA libraries of both parent and mutant strains of *H. parasuis* were denatured and subjected to cluster amplification on a Single End Flow Cell v 4 with a Cluster Generation Station instrument (Illumina) to generate raw cluster intensity of ~600,000 $mm^2$. Sequencing was performed on a Genome Analyzer GAII for 56 cycles using Sequencing Kit reagents (Illumina). The generation of sequence and downstream analysis were performed at the University of Nebraska, Lincoln genomics facility and at the University of Washington.

Comparison of Sequences:

The sequences were compared against the reported GenBank genome sequence of *H. parasuis* SH0165 (Xu et. al. "Genomic Characterization of *H. parasuis* SH0165, a Highly Virulent Strain of Serovar 5 Prevalent in China," PLoS ONE, Vol. 6, Issue 5, May 2011, www.plosone.org) and the homology was identified with known defined genes. The sequences of both the parent and mutant were compared with each other to look for any single nucleotide polymorphisms (SNPs) that occur in the coding regions of the genes. This analysis revealed several SNPs and those that resulted in the amino acid changes were considered for further verification. The SNPs that resulted in the amino acid change were verified using Sanger Sequencing technique according to established protocols.

The gsMapper software was used to analyze the SNPs between the parent vs. mutant and mutant vs. SH0165. The softwares gsMapper and newbler assembler (Genome Sequencer 20, Version 1.0.53) are proprietary softwares developed by Hoffmann-La Roche Ltd. Given two sets of raw reads (eg., readA and readB) from different genomes, the newbler assembler was used to create two independent sets of contigs, named as contigA and contigB. The contig sequence from one genome was used as a reference while the reads from the other genome were aligned based on them using gsMapper software. Specifically, two gsMapper runs were carried out, where readA was mapped to contigB in one run and readB to contigA in another run. The gsMapper software utilizes a reference sequence (SH0165) to aid the assembly of raw read data. In addition to sequence assembly, this software gives a "high confidence difference (HCD)" file that summarizes all regions, where the sequence alignment shows differences between reference and multiple read sequences spanning that region. From "readA mapped to contigB" gsMapper run, readA sequences spanning a HCD region (e.g., HCD1) were checked to identify regions within contigA sequence, where they were assembled by the previous newbler run. If this particular region also appears in the HCD output file from the "readB mapped to contigA" gsMapper run, where readB sequences spanning this HCD have been assembled to the region where the previous HCD1 is found, this HCD was considered to be an SNP. For the comparison of genomes between different isolates, each SNP analysis was supported by at least 10 reads from each genome, where at least 80% of the reads spanning that region show the difference. Finally, the SNP data is filtered based on contig base quality score (at least 60) as well as whether or not the SNP is found on a homopolymer region of 3 bases or more to reduce false positive error.

Results: Single Nucleotide Polymorphisms (SNP) Identified in the Vaccine Strain of *H. parasuis*.

The SNPs that resulted in the change of amino acid are discussed below regarding their association with virulence as seen in the literature on *H. parasuis* or related bacterial species.

The complete ORF of the gene is shown in sequence listings filed with this patent application.

TABLE 13

| | 30S ribosomal protein S12 | | |
|---|---|---|---|
| SEQ ID | SNP POSITION | NUCLEOTIDE CHANGE | AMINO ACID CHANGE |
| 1-4 | 68 | C > A | A > E |
| 1-4 | 272 | C > T | P > L |

The 30S ribosomal protein S12 plays a role in the susceptibility/resistance/dependence for streptomycin antibiotic. The above two mutations were reported to be responsible for the streptomycin dependence seen in our vaccine strain in the parent patent application.

TABLE 14

| | N-acetyl-D-glucosamine kinase | | |
|---|---|---|---|
| SEQ ID | SNP POSITION | NUCLEOTIDE CHANGE | AMINO ACID CHANGE |
| 5-8 | 456 | G > A | M > I |

N-Acetyl-L-glutamate kinase (NAGK) is involved in the metabolism of the bacteria. It plays a role in the arginine biosynthesis and also responsible for ornithine synthesis. The amino acid arginine is required for the survival of the bacteria. Previous studies have shown that mutations in nagK gene resulted in decreased arginine synthesis in *Pseudomonas aeruginosa*.

J Mol Biol. 2009 Jun. 19; 389(4):748-58. *N-acetyl-L-glutamate kinase (NAGK) from oxygenic phototrophs: P(II) signal transduction across domains of life reveals novel insights in NAGK control*. Beez S, Fokina O, Herrmann C, Forchhammer K.

J Bacteriol. 2004 November; 186(21):7273-9. *The N-acetyl-D-glucosamine kinase of Escherichia coli and its role in murein recycling*. Uehara T, Park JT.

J Bacteriol. 2008 April; 190(8):3018-25. *Basis of arginine sensitivity of microbial N-acetyl-L-glutamate kinases: mutagenesis and protein engineering study with the Pseudomonas aeruginosa and Escherichia coli enzymes*. Fernández-Murga M L, Rubio V.

TABLE 15

| | F0F1 ATP synthase subunit C | | |
|---|---|---|---|
| SEQ ID | SNP POSITION | NUCLEOTIDE CHANGE | AMINO ACID CHANGE |
| 9-12 | 188 | C > T | A > V |

ATP synthase is an enzyme involved in the synthesis of ATP, an energy molecule that is required for the metabolic activities of the bacteria. This protein is also reported to be playing a role in the antibiotic resistance of the bacteria. The new generation antibiotics are:

Nat Chem Biol. 2007 June; 3(6):323-4. *Diarylquinolines target subunit c of mycobacterial ATP synthase*. Koul A, Dendouga N, Vergauwen K, Molenberghs B, Vranckx L, Willebrords R, Ristic Z, Lill H, Dorange I, Guillemont J, Bald D, Andries K.

Because of the above determination of polynucleotide sequences in the mutant strain with the polynucleotide sequences of a known *H. parasuis* genome, and thus the conceptual determination of the protein products, Applicant expects that further experimentation will show the absence or altered function of the protein products in the mutant as compared to the parent strain. Such experiments can be carried out by methods known in the art such as enzyme assays, Western blots, immunohistochemical assays and ELISA assays.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described below. All publications, patent applications, patents, and other references mentioned herein are incorporated by reference in their entirety to the extent allowed by applicable law and regulations. In case of conflict, the present specification, including definitions, will control.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. A vaccine for protecting pigs against infection by *H. parasuis*, comprising a veterinarily acceptable carrier and an immunologically effective amount of live cells of an isolated strain of a serovar derived from a pathogenic parent strain of *H. parasuis*, wherein said cells exhibit attenuated pathogenicity in pigs as compared to those of the parent strain and wherein said cells are capable of triggering an immune response that protects the pig against *H. parasuis* infection or reduction in disease when administered as a live vaccine, wherein the parent strain and the isolated strain are serovar 5 of *H. parasuis*, wherein the vaccine provides heterologous protection against at least serovars 4 and 13; and wherein the live cells differ from the virulent parent strain in that they have mutated versions of the genes encoding the 30S ribosomal protein S12, the N-acetyl-D-glucosamine kinase, and the F0F1 ATP synthase subunit C, with respect to the corresponding genes present in the parent strain.

2. The vaccine of claim 1, wherein the isolated strain was derived from the pathogenic parent strain by MNNG mutagenesis.

3. The vaccine of claim 2, wherein the isolated strain is dependent on streptomycin for growth, said dependency being associated with a strA gene.

4. The vaccine of claim 3, wherein the DNA sequence of the strA gene of the parent strain is SEQ ID NO: 1 and wherein the DNA sequence of the strA gene of the isolated strain is SEQ ID NO: 2.

5. The vaccine of claim 4, wherein the protein encoded by the strA gene of the parent strain is SEQ ID NO: 3 and wherein the protein encoded by the strA gene of the isolated strain is SEQ ID NO: 4.

6. The vaccine of claim 5, wherein the protein encoded by DNA sequence SEQ ID NO: 1 comprises a portion of 30S ribosomal subunit S12 and the protein encoded by DNA sequence SEQ ID NO: 2 comprises at least one amino acid change in said portion of said 30S ribosomal subunit S12.

7. The vaccine of claim 4, wherein the strA gene of the isolated strain differs from the strA gene of the parent strain and wherein the difference comprises a change at nucleotide 68 from C to A and a change at nucleotide 272 from C to T.

8. The vaccine of claim 6, wherein said amino acid change comprises a change at residue 23 from alanine to glutamic acid and a change at residue 91 from proline to leucine.

9. The vaccine of claim 2, wherein SEQ ID NO: 5 comprises an open reading frame of the parent strain and wherein SEQ ID NO: 6 comprises a protein encoded by SEQ ID NO: 5 and wherein SEQ ID NO: 7 comprises an open reading frame of the isolated strain and wherein SEQ ID NO: 8 comprises a protein encoded by SEQ ID NO:7.

10. The vaccine of claim 9, wherein the protein encoded by SEQ ID NO: 5 comprises N-acetyl-D-glucosamine kinase and wherein the protein encoded by SEQ ID NO: 7 comprises N-acetyl-D-glucosamine kinase having at least one amino acid change from said protein encoded by SEQ ID NO: 5.

11. The vaccine of claim 2, wherein SEQ ID NO: 9 comprises an open reading frame of the parent strain and wherein SEQ ID NO: 10 comprises a protein encoded by SEQ ID NO: 9 and wherein SEQ ID NO: 11 comprises an open reading frame of the isolated strain and wherein SEQ ID NO: 12 comprises a protein encoded by SEQ ID NO: 11.

12. The vaccine of claim 11, wherein the protein encoded by SEQ ID NO: 9 comprises F0F1 ATP synthase subunit C and wherein the protein encoded by SEQ ID NO: 11 comprises F0F1 ATP synthase subunit C having at least one amino acid change from said protein encoded by SEQ ID NO: 9.

13. An isolated and purified DNA from the isolated strain of claim 1, said isolated and purified DNA having the nucleotide sequence set forth in SEQ ID NO: 7.

14. The isolated and purified DNA of claim 13, wherein said isolated and purified DNA codes for a polypeptide having the amino acid sequence set forth in SEQ ID NO: 8.

15. The isolated DNA of claim 14, wherein said polypeptide comprises N-acetyl-D-glucosamine kinase.

16. An isolated DNA having at least 85% homology with the DNA of claim 15.

17. An isolated and purified DNA from the isolated strain of claim 1, said isolated and purified DNA having the nucleotide sequence set forth in SEQ ID NO: 11.

18. The isolated and purified DNA of claim 17, wherein said isolated and purified DNA codes for a polypeptide having the amino acid sequence set forth in SEQ ID NO: 12.

19. The isolated and purified DNA of claim 18, wherein said polypeptide comprises F0F1 ATP synthase subunit C.

20. An isolated DNA having 85% homology with the DNA of claim 19.

21. An isolated and purified DNA from the isolated strain of claim 1, comprising a combination of SEQ ID NO: 7 and SEQ ID NO: 11.

22. An isolated and purified DNA from the isolated strain of claim 1, comprising a combination of SEQ ID NO: 2, SEQ ID NO: 7, and SEQ ID NO: 11.

\* \* \* \* \*

SEQUENCE LISTING

<160> NUMBER OF SEQ ID NOS: 14

<210> SEQ ID NO 1
<211> LENGTH: 375
<212> TYPE: DNA
<213> ORGANISM: Haemophilus parasuis

<400> SEQUENCE: 1

```
atggcaacta tcaaccagct agtacgcaaa ccgcgtgtga aaaggttgt aaaaagcaac      60
gttcctgcat tagaggcttg cccgcagaaa cgtggtgtgt gtactcgtgt atacactaca     120
actcctaaaa aaccaaactc agcgttacgt aaagtatgtc gtatccgctt aacaaacggt    180
tttgaagtaa cttcttatat cggtggtgaa ggtcacaacc ttcaagagca cagtgttgtg    240
ttaatccgtg gtggtcgtgt aaagactta ccgggtgtgc gttatcacac tgtacgtggt     300
gcacttgact gtgcaggcgt taaagaccgt aaacaaggtc gttctaaata cggcgttaaa    360
cgtcctaagt cttaa                                                      375
```

<210> SEQ ID NO 2
<211> LENGTH: 375
<212> TYPE: DNA
<213> ORGANISM: Haemophilus parasuis

<400> SEQUENCE: 2

```
atggcaacta tcaaccagct agtacgcaaa ccgcgtgtga aaaggttgt aaaaagcaac      60
gttcctgaat tagaggcttg cccgcagaaa cgtggtgtgt gtactcgtgt atacactaca    120
actcctaaaa aaccaaactc agcgttacgt aaagtatgtc gtatccgctt aacaaacggt    180
tttgaagtaa cttcttatat cggtggtgaa ggtcacaacc ttcaagagca cagtgttgtg    240
ttaatccgtg gtggtcgtgt aaagactta ctgggtgtgc gttatcacac tgtacgtggt     300
gcacttgact gtgcaggcgt taaagaccgt aaacaaggtc gttctaaata cggcgttaaa    360
cgtcctaagt cttaa                                                      375
```

<210> SEQ ID NO 3
<211> LENGTH: 124
<212> TYPE: PRT
<213> ORGANISM: Haemophilus parasuis

<400> SEQUENCE: 3

```
Met Ala Thr Ile Asn Gln Leu Val Arg Lys Pro Arg Val Lys Lys Val
1               5                   10                  15

Val Lys Ser Asn Val Pro Ala Leu Glu Ala Cys Pro Gln Lys Arg Gly
                20                  25                  30

Val Cys Thr Arg Val Tyr Thr Thr Thr Pro Lys Lys Pro Asn Ser Ala
            35                  40                  45

Leu Arg Lys Val Cys Arg Ile Arg Leu Thr Asn Gly Phe Glu Val Thr
        50                  55                  60

Ser Tyr Ile Gly Gly Glu Gly His Asn Leu Gln Glu His Ser Val Val
65                  70                  75                  80

Leu Ile Arg Gly Gly Arg Val Lys Asp Leu Pro Gly Val Arg Tyr His
                85                  90                  95

Thr Val Arg Gly Ala Leu Asp Cys Ala Gly Val Lys Asp Arg Lys Gln
            100                 105                 110

Gly Arg Ser Lys Tyr Gly Val Lys Arg Pro Lys Ser
        115                 120
```

<210> SEQ ID NO 4
<211> LENGTH: 124
<212> TYPE: PRT
<213> ORGANISM: Haemophilus parasuis

<400> SEQUENCE: 4

Met Ala Thr Ile Asn Gln Leu Val Arg Lys Pro Arg Val Lys Lys Val
1               5                   10                  15

Val Lys Ser Asn Val Pro Glu Leu Glu Ala Cys Pro Gln Lys Arg Gly
            20                  25                  30

Val Cys Thr Arg Val Tyr Thr Thr Thr Pro Lys Lys Pro Asn Ser Ala
        35                  40                  45

Leu Arg Lys Val Cys Arg Ile Arg Leu Thr Asn Gly Phe Glu Val Thr
    50                  55                  60

Ser Tyr Ile Gly Gly Glu Gly His Asn Leu Gln Glu His Ser Val Val
65                  70                  75                  80

Leu Ile Arg Gly Gly Arg Val Lys Asp Leu Leu Gly Val Arg Tyr His
                85                  90                  95

Thr Val Arg Gly Ala Leu Asp Cys Ala Gly Val Lys Asp Arg Lys Gln
            100                 105                 110

Gly Arg Ser Lys Tyr Gly Val Lys Arg Pro Lys Ser
        115                 120

<210> SEQ ID NO 5
<211> LENGTH: 915
<212> TYPE: DNA
<213> ORGANISM: Haemophilus parasuis

<400> SEQUENCE: 5
atggtttatt acggtttgga tattggcggt acaaaaattg aattggctgc ctttaatgag      60
aaattagaga agttacacag cgagcgagtg ccaaccccac aaacgagtta tgaggattgg     120
ttaagaacag tggaaacctt agtgcgtaat gccgatgcaa aatttggcga gtacggcact     180
gtggggcttg gtgtaccagg ttttgttaat cataaaactg ggttagcgga aattgccaac     240
attgcggtgg ttcatggcaa taaaattatt caagatttgg aagcgcgttt agggcgtgaa     300
gtgcgtgttg aaaacgatgc gaactgcttg gctttatcgg aagcgtggga cgaaagcaat     360
ctgcaatatt caacggtgtt agggttgatt attggtacag ttttggtgg cggtattgtg      420 ttgaacggta aagctcactc aggtcaaatc ggtatggctg cgaggtggg gcatattcag      480 cttaactacc acgcgttgaa attgcttggt tgggataagg caccgattta taatgtggc      540 tgtggtaata tggcttgttt ggatagctat atctcaggac gtggttttga gatgctttat     600
aatgatttag tcggcgaaaa agttgatgca aaaaacatta ttcagcgttt ttacgataaa     660
gatgagaaaa ccgttgagtt tgttgagaaa tacattgagt taatggcaat ttcggtggca     720
aattatatta cggtacttga tccagatatg attgtgtttg gtggtggttt gtctaacttt     780
gattatattt atgaagcctt gccaaaagcc ttaccaaaat attttattgcg taatacggaa     840 gtgccagtga ttaaaaaagc gatccacggt gactcaagcg gtgtgcgtgg ggcggcagcg     900
ttattcttga aatag                                                      915

<210> SEQ ID NO 6
<211> LENGTH: 304
<212> TYPE: PRT
<213> ORGANISM: Haemophilus parasuis

<400> SEQUENCE: 6

```
Met Val Tyr Tyr Gly Leu Asp Ile Gly Gly Thr Lys Ile Glu Leu Ala
1               5                   10                  15

Ala Phe Asn Glu Lys Leu Glu Lys Leu His Ser Glu Arg Val Pro Thr
            20                  25                  30

Pro Gln Thr Ser Tyr Glu Asp Trp Leu Arg Thr Val Glu Thr Leu Val
            35                  40                  45

Arg Asn Ala Asp Ala Lys Phe Gly Glu Tyr Gly Thr Val Gly Leu Gly
50                  55                  60

Val Pro Gly Phe Val Asn His Lys Thr Gly Leu Ala Glu Ile Ala Asn
65                  70                  75                  80

Ile Ala Val Val His Gly Asn Lys Ile Ile Gln Asp Leu Glu Ala Arg
                85                  90                  95

Leu Gly Arg Glu Val Arg Val Glu Asn Asp Ala Asn Cys Leu Ala Leu
            100                 105                 110

Ser Glu Ala Trp Asp Glu Ser Asn Leu Gln Tyr Ser Thr Val Leu Gly
            115                 120                 125

Leu Ile Ile Gly Thr Gly Phe Gly Gly Gly Ile Val Leu Asn Gly Lys
            130                 135                 140

Ala His Ser Gly Gln Ile Gly Met Ala Gly Glu Val Gly His Ile Gln
145                 150                 155                 160

Leu Asn Tyr His Ala Leu Lys Leu Leu Gly Trp Asp Lys Ala Pro Ile
                165                 170                 175

Tyr Lys Cys Gly Cys Gly Asn Met Ala Cys Leu Asp Ser Tyr Ile Ser
            180                 185                 190

Gly Arg Gly Phe Glu Met Leu Tyr Asn Asp Leu Val Gly Glu Lys Val
            195                 200                 205

Asp Ala Lys Asn Ile Ile Gln Arg Phe Tyr Asp Lys Asp Glu Lys Thr
210                 215                 220

Val Glu Phe Val Glu Lys Tyr Ile Glu Leu Met Ala Ile Ser Val Ala
225                 230                 235                 240

Asn Tyr Ile Thr Val Leu Asp Pro Asp Met Ile Val Phe Gly Gly Gly
                245                 250                 255

Leu Ser Asn Phe Asp Tyr Ile Tyr Glu Ala Leu Pro Lys Ala Leu Pro
            260                 265                 270

Lys Tyr Leu Leu Arg Asn Thr Glu Val Pro Val Ile Lys Lys Ala Ile
            275                 280                 285

His Gly Asp Ser Ser Gly Val Arg Gly Ala Ala Ala Leu Phe Leu Lys
            290                 295                 300
```

<210> SEQ ID NO 7
<211> LENGTH: 915
<212> TYPE: DNA
<213> ORGANISM: Haemophilus parasuis

<400> SEQUENCE: 7

```
atggtttatt acggtttgga tattggcggt acaaaaattg aattggctgc ctttaatgag      60
aaattagaga agttacacag cgagcgagtg ccaaccccac aaacgagtta tgaggattgg     120
ttaagaacag tggaaacctt agtgcgtaat gccgatgcaa aatttggcga gtacggcact     180
gtggggcttg gtgtaccagg ttttgttaat cataaaactg gttagcgga  aattgccaac     240 attgcggtgg ttcatggcaa taaaattatt caagatttgg aagcgcgttt agggcgtgaa     300
gtgcgtgttg aaaacgatgc gaactgcttg gctttatcgg aagcgtggga cgaaagcaat     360
ctgcaatatt caacggtgtt agggttgatt attggtacag ttttggtgg cggtattgtg     420
```

-continued

```
ttgaacggta aagctcactc aggtcaaatc ggtatagctg cgaggtggg gcatattcag    480 cttaactacc acgcgttgaa attgcttggt tgggataagg caccgattta taaatgtggc    540
tgtggtaata tggcttgttt ggatagctat atctcaggac gtggttttga gatgctttat    600
aatgatttag tcggcgaaaa agttgatgca aaaaacatta ttcagcgttt ttacgataaa    660
gatgagaaaa ccgttgagtt tgttgagaaa tacattgagt taatggcaat ttcggtggca    720
aattatatta cggtacttga tccagatatg attgtgtttg gtggtggttt gtctaacttt    780
gattatattt atgaagcctt gccaaaagcc ttaccaaaat atttattgcg taatacggaa    840
gtgccagtga ttaaaaaagc gatccacggt gactcaagcg gtgtgcgtgg ggcggcagcg    900
ttattcttga aatag                                                     915
```

<210> SEQ ID NO 8
<211> LENGTH: 304
<212> TYPE: PRT
<213> ORGANISM: Haemophilus parasuis

<400> SEQUENCE: 8

```
Met Val Tyr Tyr Gly Leu Asp Ile Gly Gly Thr Lys Ile Glu Leu Ala
1               5                  10                  15

Ala Phe Asn Glu Lys Leu Glu Lys Leu His Ser Glu Arg Val Pro Thr
                20                  25                  30

Pro Gln Thr Ser Tyr Glu Asp Trp Leu Arg Thr Val Glu Thr Leu Val
            35                  40                  45

Arg Asn Ala Asp Ala Lys Phe Gly Glu Tyr Gly Thr Val Gly Leu Gly
        50                  55                  60

Val Pro Gly Phe Val Asn His Lys Thr Gly Leu Ala Glu Ile Ala Asn
65                  70                  75                  80

Ile Ala Val Val His Gly Asn Lys Ile Ile Gln Asp Leu Glu Ala Arg
                85                  90                  95

Leu Gly Arg Glu Val Arg Val Glu Asn Asp Ala Asn Cys Leu Ala Leu
                100                 105                 110

Ser Glu Ala Trp Asp Glu Ser Asn Leu Gln Tyr Ser Thr Val Leu Gly
            115                 120                 125

Leu Ile Ile Gly Thr Gly Phe Gly Gly Gly Ile Val Leu Asn Gly Lys
        130                 135                 140

Ala His Ser Gly Gln Ile Gly Ile Ala Gly Glu Val Gly His Ile Gln
145                 150                 155                 160

Leu Asn Tyr His Ala Leu Lys Leu Leu Gly Trp Asp Lys Ala Pro Ile
                165                 170                 175

Tyr Lys Cys Gly Cys Gly Asn Met Ala Cys Leu Asp Ser Tyr Ile Ser
            180                 185                 190

Gly Arg Gly Phe Glu Met Leu Tyr Asn Asp Leu Val Gly Glu Lys Val
        195                 200                 205

Asp Ala Lys Asn Ile Ile Gln Arg Phe Tyr Asp Lys Asp Glu Lys Thr
    210                 215                 220

Val Glu Phe Val Glu Lys Tyr Ile Glu Leu Met Ala Ile Ser Val Ala
225                 230                 235                 240

Asn Tyr Ile Thr Val Leu Asp Pro Asp Met Ile Val Phe Gly Gly Gly
                245                 250                 255

Leu Ser Asn Phe Asp Tyr Ile Tyr Glu Ala Leu Pro Lys Ala Leu Pro
            260                 265                 270

Lys Tyr Leu Leu Arg Asn Thr Glu Val Pro Val Ile Lys Lys Ala Ile
        275                 280                 285
```

His Gly Asp Ser Ser Gly Val Arg Gly Ala Ala Ala Leu Phe Leu Lys
            290                 295                 300

<210> SEQ ID NO 9
<211> LENGTH: 255
<212> TYPE: DNA
<213> ORGANISM: Haemophilus parasuis

<400> SEQUENCE: 9
atggaaactg taattacagc aactattatt ggcgcatcaa tcctacttgc tttcgcagca      60
ttaggtactg caattggctt cgctatctta ggtggtaaat tcttagagtc ttcagctcgt     120
caaccagaat tagcaagcag cttacaaact aaaatgttta tcgttgcagg tcttttagat     180
gcgattgcaa tgattgcagt aggtatttct ttactttca tcttcgcaaa cccgttcatt      240
gatttattga aataa                                                      255

<210> SEQ ID NO 10
<211> LENGTH: 84
<212> TYPE: PRT
<213> ORGANISM: Haemophilus parasuis

<400> SEQUENCE: 10

Met Glu Thr Val Ile Thr Ala Thr Ile Ile Gly Ala Ser Ile Leu Leu
1               5                   10                  15

Ala Phe Ala Ala Leu Gly Thr Ala Ile Gly Phe Ala Ile Leu Gly Gly
            20                  25                  30

Lys Phe Leu Glu Ser Ser Ala Arg Gln Pro Glu Leu Ala Ser Ser Leu
        35                  40                  45

Gln Thr Lys Met Phe Ile Val Ala Gly Leu Leu Asp Ala Ile Ala Met
    50                  55                  60

Ile Ala Val Gly Ile Ser Leu Leu Phe Ile Phe Ala Asn Pro Phe Ile
65                  70                  75                  80

Asp Leu Leu Lys

<210> SEQ ID NO 11
<211> LENGTH: 255
<212> TYPE: DNA
<213> ORGANISM: Haemophilus parasuis

<400> SEQUENCE: 11
atggaaactg taattacagc aactattatt ggcgcatcaa tcctacttgc tttcgcagca      60
ttaggtactg caattggctt cgctatctta ggtggtaaat tcttagagtc ttcagctcgt     120
caaccagaat tagcaagcag cttacaaact aaaatgttta tcgttgcagg tcttttagat     180
gcgattgtaa tgattgcagt aggtatttct ttactttca tcttcgcaaa cccgttcatt      240
gatttattga aataa                                                      255

<210> SEQ ID NO 12
<211> LENGTH: 84
<212> TYPE: PRT
<213> ORGANISM: Haemophilus parasuis

<400> SEQUENCE: 12

Met Glu Thr Val Ile Thr Ala Thr Ile Ile Gly Ala Ser Ile Leu Leu
1               5                   10                  15

Ala Phe Ala Ala Leu Gly Thr Ala Ile Gly Phe Ala Ile Leu Gly Gly
            20                  25                  30

```
Lys Phe Leu Glu Ser Ser Ala Arg Gln Pro Glu Leu Ala Ser Ser Leu
        35                  40                  45

Gln Thr Lys Met Phe Ile Val Ala Gly Leu Leu Asp Ala Ile Val Met
    50                  55                  60

Ile Ala Val Gly Ile Ser Leu Leu Phe Ile Phe Ala Asn Pro Phe Ile
65                  70                  75                  80

Asp Leu Leu Lys

<210> SEQ ID NO 13
<211> LENGTH: 18
<212> TYPE: DNA
<213> ORGANISM: Artificial Sequence
<220> FEATURE:
<223> OTHER INFORMATION: strA Forward primer

<400> SEQUENCE: 13
tacgcaaacc gcgtgtga                                             18

<210> SEQ ID NO 14
<211> LENGTH: 20
<212> TYPE: DNA
<213> ORGANISM: Artificial Sequence
<220> FEATURE:
<223> OTHER INFORMATION: strA Reverse primer

<400> SEQUENCE: 14
tgcgtgcttc aacactacga                                           20
```